(12) United States Patent
Cantrall et al.

(10) Patent No.: US 11,625,825 B2
(45) Date of Patent: Apr. 11, 2023

(54) METHOD FOR DISPLAYING TUMOR LOCATION WITHIN ENDOSCOPIC IMAGES

(71) Applicant: COVIDIEN LP, Mansfield, MA (US)

(72) Inventors: Irena Cantrall, Boulder, CO (US); John W. Komp, Dillon, CO (US); Francesca Rossetto, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 435 days.

(21) Appl. No.: 16/718,815

(22) Filed: Dec. 18, 2019

(65) Prior Publication Data

US 2020/0237187 A1 Jul. 30, 2020

Related U.S. Application Data

(60) Provisional application No. 62/798,854, filed on Jan. 30, 2019.

(51) Int. Cl.
*G06T 7/00* (2017.01)
*A61B 1/00* (2006.01)
*A61B 1/06* (2006.01)

(52) U.S. Cl.
CPC ........ *G06T 7/0012* (2013.01); *A61B 1/00045* (2013.01); *A61B 1/00147* (2013.01);
(Continued)

(58) Field of Classification Search
CPC ............ A61B 1/00009; A61B 1/00045; A61B 1/00147; A61B 1/00163; A61B 1/045;
(Continued)

(56) References Cited

U.S. PATENT DOCUMENTS

| 4,932,412 A | 6/1990 | Goldenberg |
| 5,057,494 A | 10/1991 | Sheffield |

(Continued)

FOREIGN PATENT DOCUMENTS

| BR | 0013237 A | 7/2003 |
| BR | 0116004 A | 6/2004 |

(Continued)

*Primary Examiner* — Aaron B Fairchild
*Assistant Examiner* — Julianna J Nicolaus
(74) *Attorney, Agent, or Firm* — Weber Rosselli & Cannon LLP

(57) ABSTRACT

A method of displaying an area of interest within a surgical site includes modeling a patient's lungs and identifying a location of an area of interest within the model of the patient's lungs. The topography of the surface of the patient's lungs is determined using an endoscope having a first camera, a light source, and a structured light pattern source. Real-time images of the patient's lungs are displayed on a monitor and the real-time images are registered to the model of the patient's lungs using the determined topography of the patient's lungs. A marker indicative of the location of the area of interest is superimposed over the real-time images of the patient's lungs. If the marker falls outside of the field-of view of the endoscope, an arrow is superimposed over the real-time images to indicate the direction in which the marker is located relative to the field of view.

20 Claims, 10 Drawing Sheets

(52) U.S. Cl.
CPC ........ *A61B 1/0676* (2013.01); *A61B 1/00194* (2022.02); *G06T 2207/10068* (2013.01); *G06T 2207/10081* (2013.01); *G06T 2207/30061* (2013.01); *G06T 2211/428* (2013.01)

(58) Field of Classification Search
CPC ... A61B 1/05; A61B 1/0676; A61B 2090/367; A61B 2090/368; G06T 2207/10068; G06T 2207/10081; G06T 2207/30061; G06T 2207/20104; G06T 7/0012; H04N 5/2251; H04N 2205/2255
See application file for complete search history.

(56) References Cited

U.S. PATENT DOCUMENTS

| | | |
|---|---|---|
| 5,318,024 A | 6/1994 | Kittrell et al. |
| 5,321,113 A | 6/1994 | Cooper et al. |
| 5,697,897 A | 12/1997 | Buchholtz et al. |
| 5,716,595 A | 2/1998 | Goldenberg |
| 5,827,190 A | 10/1998 | Palcic et al. |
| 5,879,284 A | 3/1999 | Tsujita |
| 6,003,517 A | 12/1999 | Sheffield et al. |
| 6,096,289 A | 8/2000 | Goldenberg |
| 6,284,223 B1 | 9/2001 | Luiken |
| 6,293,911 B1 | 9/2001 | Imaizumi et al. |
| 6,346,940 B1 | 2/2002 | Fukunaga |
| 6,364,831 B1 | 4/2002 | Crowley |
| 6,387,350 B2 | 5/2002 | Goldenberg |
| 6,388,702 B1 | 5/2002 | Konomura et al. |
| 6,498,948 B1 | 12/2002 | Ozawa et al. |
| 6,537,211 B1 | 3/2003 | Wang et al. |
| 6,652,836 B2 | 11/2003 | Luiken |
| 6,863,536 B1 | 3/2005 | Fisher et al. |
| 6,871,086 B2 | 3/2005 | Nevo et al. |
| 6,984,211 B2 | 1/2006 | Hao et al. |
| 7,179,222 B2 | 2/2007 | Imaizumi et al. |
| 7,201,890 B2 | 4/2007 | Goldenberg |
| 7,226,412 B2 | 6/2007 | Ueno et al. |
| 7,235,045 B2 | 6/2007 | Wang et al. |
| 7,381,183 B2 | 6/2008 | Hale et al. |
| 7,822,461 B2 | 10/2010 | Geiger et al. |
| 7,901,348 B2 | 3/2011 | Soper et al. |
| 8,169,468 B2 | 5/2012 | Scott et al. |
| 8,251,893 B2 | 8/2012 | Yamamoto et al. |
| 8,289,381 B2 | 10/2012 | Bayer et al. |
| 8,335,359 B2 | 12/2012 | Fidrich et al. |
| 8,337,397 B2 | 12/2012 | Prisco et al. |
| 8,337,399 B2 | 12/2012 | Sugimoto et al. |
| 8,382,662 B2 | 2/2013 | Soper et al. |
| 8,403,828 B2 | 3/2013 | Mawn et al. |
| 8,419,628 B2 | 4/2013 | Suzuki et al. |
| 8,498,695 B2 | 7/2013 | Westwick et al. |
| 8,535,218 B2 | 9/2013 | Konno |
| 8,579,799 B2 | 11/2013 | Yamaguchi et al. |
| 8,585,586 B2 | 11/2013 | Yamaguchi et al. |
| 8,630,698 B2 | 1/2014 | Fengler et al. |
| 8,672,836 B2 | 3/2014 | Higgins et al. |
| 8,706,184 B2 | 4/2014 | Mohr et al. |
| 8,758,234 B2 | 6/2014 | Hale et al. |
| 8,771,177 B2 | 7/2014 | Hale et al. |
| 8,814,782 B2 | 8/2014 | Hale et al. |
| 8,827,934 B2 | 9/2014 | Chopra et al. |
| 8,848,987 B2 | 9/2014 | Nölle et al. |
| 8,870,750 B2 | 10/2014 | Fehre et al. |
| 8,872,906 B2 | 10/2014 | Bayer et al. |
| 8,917,319 B2 | 12/2014 | Igarashi et al. |
| 8,992,423 B2 | 3/2015 | Hale et al. |
| 9,055,881 B2 | 6/2015 | Gilboa et al. |
| 9,111,335 B2 | 8/2015 | Kaku |
| 9,113,814 B2 | 8/2015 | Choe et al. |
| 9,143,746 B2 | 9/2015 | Westwick et al. |
| 9,173,632 B2 | 11/2015 | Shiki et al. |
| 9,179,822 B2 | 11/2015 | Kitamura et al. |
| 9,204,781 B2 | 12/2015 | Taniguchi |
| 9,220,399 B2 | 12/2015 | Cinquin et al. |
| 9,220,468 B2 | 12/2015 | Kitamura et al. |
| 9,375,133 B2 | 6/2016 | Kitamura et al. |
| 9,375,268 B2 | 6/2016 | Long |
| 9,386,908 B2 | 7/2016 | Finkman et al. |
| 9,414,741 B2 | 8/2016 | Yamamoto |
| 9,510,739 B2 | 12/2016 | Adler |
| 9,521,944 B2 | 12/2016 | Minamizato et al. |
| 9,545,220 B2 | 1/2017 | Sidlesky |
| 9,549,667 B2 | 1/2017 | Manohara et al. |
| 9,560,953 B2 | 2/2017 | Gilreath et al. |
| 9,603,508 B2 | 3/2017 | Hale et al. |
| 9,619,938 B2 | 4/2017 | Itai |
| 9,691,162 B2 | 6/2017 | Christiansen |
| 9,763,563 B2 | 9/2017 | Hoeg et al. |
| 9,865,079 B2 | 1/2018 | Miyamoto |
| 9,918,659 B2 | 3/2018 | Chopra et al. |
| 9,986,890 B2 | 6/2018 | Miyai |
| 9,986,892 B2 | 6/2018 | Gilreath et al. |
| 9,999,343 B2 | 6/2018 | Morimoto et al. |
| 10,004,387 B2 | 6/2018 | Prisco |
| 10,004,558 B2 | 6/2018 | Long |
| 10,045,685 B2 | 8/2018 | Bayer et al. |
| 10,092,169 B2 | 10/2018 | Hale et al. |
| 10,182,709 B2 | 1/2019 | Fengler et al. |
| 10,182,791 B2 | 1/2019 | Zhou et al. |
| 10,194,897 B2 | 2/2019 | Cedro et al. |
| 10,278,568 B2 | 5/2019 | Manohara et al. |
| 10,321,803 B2 | 6/2019 | Gilboa et al. |
| 10,368,725 B2 | 8/2019 | Uemori |
| 10,373,719 B2 | 8/2019 | Soper et al. |
| 10,376,178 B2 | 8/2019 | Chopra |
| 10,405,753 B2 | 9/2019 | Sorger |
| 10,413,159 B2 | 9/2019 | Steffen et al. |
| 10,426,318 B2 | 10/2019 | Kamon |
| 10,426,345 B2 | 10/2019 | Shekhar et al. |
| 10,478,092 B2 | 11/2019 | Averbuch et al. |
| 10,478,162 B2 | 11/2019 | Barbagli et al. |
| 10,480,926 B2 | 11/2019 | Froggatt et al. |
| 10,482,313 B2 | 11/2019 | Murthy et al. |
| 10,492,671 B2 | 12/2019 | Carroll et al. |
| 10,499,794 B2 | 12/2019 | Gilreath et al. |
| 10,510,144 B2 | 12/2019 | Zur |
| 10,524,641 B2 | 1/2020 | Prisco |
| 10,524,866 B2 | 1/2020 | Srinivasan et al. |
| 10,555,788 B2 | 2/2020 | Panescu et al. |
| 10,561,338 B2 | 2/2020 | Wang |
| 10,569,071 B2 | 2/2020 | Harris et al. |
| 10,575,718 B2 | 3/2020 | Fukuda |
| 10,580,157 B2 | 3/2020 | Wang et al. |
| 10,603,106 B2 | 3/2020 | Weide et al. |
| 10,610,088 B2 | 4/2020 | Myung et al. |
| 10,610,306 B2 | 4/2020 | Chopra |
| 10,614,555 B2 | 4/2020 | Fukazawa et al. |
| 10,617,339 B2 | 4/2020 | Yamaguchi et al. |
| 10,638,953 B2 | 5/2020 | Duindam et al. |
| 10,639,114 B2 | 5/2020 | Schuh et al. |
| 10,653,295 B2 | 5/2020 | Ebata |
| 10,672,123 B2 | 6/2020 | Imai |
| 10,674,891 B2 | 6/2020 | Blohm et al. |
| 10,674,936 B2 | 6/2020 | Averbuch et al. |
| 10,674,970 B2 | 6/2020 | Averbuch et al. |
| 10,682,070 B2 | 6/2020 | Duindam |
| 10,702,137 B2 | 7/2020 | Deyanov |
| 10,706,543 B2 | 7/2020 | Donhowe et al. |
| 10,709,506 B2 | 7/2020 | Coste-Maniere et al. |
| 10,772,485 B2 | 9/2020 | Schlesinger et al. |
| 10,796,432 B2 | 10/2020 | Mintz et al. |
| 10,823,627 B2 | 11/2020 | Sanborn et al. |
| 10,827,913 B2 | 11/2020 | Ummalaneni et al. |
| 10,835,153 B2 | 11/2020 | Rafii-Tari et al. |
| 10,885,630 B2 | 1/2021 | Li et al. |
| 2002/0147462 A1 | 10/2002 | Mair et al. |
| 2003/0013972 A1 | 1/2003 | Makin |
| 2004/0120981 A1 | 6/2004 | Nathan |
| 2006/0252057 A1 | 11/2006 | Raponi et al. |
| 2008/0045938 A1 | 2/2008 | Weide et al. |
| 2013/0303945 A1 | 11/2013 | Blumenkranz et al. |
| 2014/0035798 A1 | 2/2014 | Kawada et al. |

(56) References Cited

U.S. PATENT DOCUMENTS

| | | |
|---|---|---|
| 2015/0148690 A1 | 5/2015 | Chopra et al. |
| 2015/0265368 A1 | 9/2015 | Chopra et al. |
| 2016/0157939 A1 | 6/2016 | Larkin et al. |
| 2016/0183841 A1 | 6/2016 | Duindam et al. |
| 2016/0192860 A1 | 7/2016 | Allenby et al. |
| 2016/0287344 A1 | 10/2016 | Donhowe et al. |
| 2017/0112571 A1 | 4/2017 | Thiel et al. |
| 2017/0112576 A1 | 4/2017 | Coste-Maniere et al. |
| 2017/0172382 A1* | 6/2017 | Nir .................. A61B 1/00009 |
| 2017/0209071 A1 | 7/2017 | Zhao et al. |
| 2017/0265952 A1 | 9/2017 | Donhowe et al. |
| 2017/0280970 A1* | 10/2017 | Sartor ............... G02B 23/2415 |
| 2017/0311844 A1 | 11/2017 | Zhao et al. |
| 2017/0319165 A1 | 11/2017 | Averbuch |
| 2018/0020932 A1* | 1/2018 | Chen .................... A61B 5/0261 |
| | | 600/479 |
| 2018/0078318 A1 | 3/2018 | Barbagli et al. |
| 2018/0144092 A1 | 5/2018 | Flitsch et al. |
| 2018/0153621 A1 | 6/2018 | Duindam et al. |
| 2018/0235709 A1 | 8/2018 | Donhowe et al. |
| 2018/0240237 A1 | 8/2018 | Donhowe et al. |
| 2018/0256262 A1 | 9/2018 | Duindam et al. |
| 2018/0263706 A1 | 9/2018 | Averbuch |
| 2018/0279852 A1 | 10/2018 | Rafii-Tari et al. |
| 2018/0325419 A1 | 11/2018 | Zhao et al. |
| 2019/0000559 A1 | 1/2019 | Berman et al. |
| 2019/0000560 A1 | 1/2019 | Berman et al. |
| 2019/0008413 A1 | 1/2019 | Duindam et al. |
| 2019/0038365 A1 | 2/2019 | Soper et al. |
| 2019/0065209 A1 | 2/2019 | Mishra et al. |
| 2019/0105007 A1* | 4/2019 | Kedmi-Shahar ......... A61B 6/12 |
| 2019/0110839 A1 | 4/2019 | Rafii-Tari et al. |
| 2019/0175062 A1 | 6/2019 | Rafii-Tari et al. |
| 2019/0175799 A1 | 6/2019 | Hsu et al. |
| 2019/0183318 A1 | 6/2019 | Froggatt et al. |
| 2019/0183585 A1 | 6/2019 | Rafii-Tari et al. |
| 2019/0183587 A1 | 6/2019 | Rafii-Tari et al. |
| 2019/0192234 A1 | 6/2019 | Gadda et al. |
| 2019/0209016 A1 | 7/2019 | Herzlinger et al. |
| 2019/0209043 A1 | 7/2019 | Zhao et al. |
| 2019/0216548 A1 | 7/2019 | Ummalaneni |
| 2019/0231220 A1* | 8/2019 | Refai .................. H04N 5/22541 |
| 2019/0239723 A1 | 8/2019 | Duindam et al. |
| 2019/0239831 A1 | 8/2019 | Chopra |
| 2019/0250050 A1 | 8/2019 | Sanborn et al. |
| 2019/0254649 A1 | 8/2019 | Walters et al. |
| 2019/0269470 A1 | 9/2019 | Barbagli et al. |
| 2019/0269818 A1 | 9/2019 | Dhanaraj et al. |
| 2019/0269819 A1 | 9/2019 | Dhanaraj et al. |
| 2019/0272634 A1 | 9/2019 | Li et al. |
| 2019/0298160 A1 | 10/2019 | Ummalaneni et al. |
| 2019/0298451 A1 | 10/2019 | Wong et al. |
| 2019/0320878 A1 | 10/2019 | Duindam et al. |
| 2019/0320937 A1 | 10/2019 | Duindam et al. |
| 2019/0336238 A1 | 11/2019 | Yu et al. |
| 2019/0343424 A1 | 11/2019 | Blumenkranz et al. |
| 2019/0350659 A1 | 11/2019 | Wang et al. |
| 2019/0365199 A1 | 12/2019 | Zhao et al. |
| 2019/0365479 A1 | 12/2019 | Rafii-Tari |
| 2019/0365486 A1 | 12/2019 | Srinivasan et al. |
| 2019/0380787 A1 | 12/2019 | Ye et al. |
| 2020/0000319 A1 | 1/2020 | Saadat et al. |
| 2020/0000526 A1 | 1/2020 | Zhao |
| 2020/0008655 A1 | 1/2020 | Schlesinger et al. |
| 2020/0015907 A1* | 1/2020 | Scheib ............... A61B 1/00006 |
| 2020/0030044 A1 | 1/2020 | Wang et al. |
| 2020/0030461 A1 | 1/2020 | Sorger |
| 2020/0038750 A1 | 2/2020 | Kojima |
| 2020/0043207 A1 | 2/2020 | Lo et al. |
| 2020/0046431 A1 | 2/2020 | Soper et al. |
| 2020/0046436 A1 | 2/2020 | Tzeisler et al. |
| 2020/0054399 A1 | 2/2020 | Duindam et al. |
| 2020/0054408 A1 | 2/2020 | Schuh et al. |
| 2020/0060771 A1 | 2/2020 | Lo et al. |
| 2020/0069192 A1 | 3/2020 | Sanborn et al. |
| 2020/0077870 A1 | 3/2020 | Dicarlo et al. |
| 2020/0078023 A1 | 3/2020 | Cedro et al. |
| 2020/0078095 A1 | 3/2020 | Chopra et al. |
| 2020/0078103 A1 | 3/2020 | Duindam et al. |
| 2020/0085514 A1 | 3/2020 | Blumenkranz |
| 2020/0109124 A1 | 4/2020 | Pomper et al. |
| 2020/0129045 A1 | 4/2020 | Prisco |
| 2020/0129239 A1 | 4/2020 | Bianchi et al. |
| 2020/0138514 A1 | 5/2020 | Blumenkranz et al. |
| 2020/0138515 A1 | 5/2020 | Wong |
| 2020/0142013 A1 | 5/2020 | Wong |
| 2020/0155116 A1 | 5/2020 | Donhowe et al. |
| 2020/0155232 A1 | 5/2020 | Wong |
| 2020/0170623 A1 | 6/2020 | Averbuch |
| 2020/0170720 A1 | 6/2020 | Ummalaneni |
| 2020/0179058 A1 | 6/2020 | Barbagli et al. |
| 2020/0188021 A1 | 6/2020 | Wong et al. |
| 2020/0188038 A1 | 6/2020 | Donhowe et al. |
| 2020/0205903 A1 | 7/2020 | Srinivasan et al. |
| 2020/0205904 A1 | 7/2020 | Chopra |
| 2020/0214664 A1 | 7/2020 | Zhao et al. |
| 2020/0229679 A1 | 7/2020 | Zhao et al. |
| 2020/0242767 A1 | 7/2020 | Zhao et al. |
| 2020/0275860 A1 | 9/2020 | Duindam |
| 2020/0297433 A1* | 9/2020 | Meagher ................ A61B 34/10 |
| 2020/0297442 A1 | 9/2020 | Adebar et al. |
| 2020/0315554 A1 | 10/2020 | Averbuch et al. |
| 2020/0330795 A1 | 10/2020 | Sawant et al. |
| 2020/0352427 A1 | 11/2020 | Deyanov |
| 2020/0364865 A1 | 11/2020 | Donhowe et al. |
| 2020/0383750 A1 | 12/2020 | Kemp et al. |
| 2021/0000524 A1 | 1/2021 | Barry et al. |
| 2021/0137621 A1* | 5/2021 | Ummalaneni ......... A61B 34/37 |
| 2021/0290315 A1* | 9/2021 | Lampert ............... A61B 6/032 |
| 2021/0290319 A1* | 9/2021 | Poltaretskyi ......... A61B 90/361 |

FOREIGN PATENT DOCUMENTS

| | | |
|---|---|---|
| BR | 0307259 A | 12/2004 |
| BR | 0412298 A2 | 9/2006 |
| BR | 112018003862 A2 | 10/2018 |
| CZ | 1644519 | 12/2008 |
| CZ | 486540 | 9/2016 |
| CZ | 2709512 | 8/2017 |
| CZ | 2884879 | 1/2020 |
| EP | 1644519 B1 | 12/2008 |
| EP | 2141497 A1 | 1/2010 |
| EP | 3413830 A4 | 9/2019 |
| EP | 3478161 A4 | 2/2020 |
| EP | 3641686 A2 | 4/2020 |
| EP | 3644885 A1 | 5/2020 |
| EP | 3644886 A1 | 5/2020 |
| EP | 3749239 A1 | 12/2020 |
| MX | PA03005028 A | 1/2004 |
| MX | PA03000137 A | 9/2004 |
| MX | PA03006874 A | 9/2004 |
| MX | 225663 B | 1/2005 |
| MX | 226292 | 2/2005 |
| MX | PA03010507 A | 7/2005 |
| MX | PA05011725 A | 5/2006 |
| MX | 06011286 | 3/2007 |
| MX | 246862 B | 6/2007 |
| MX | 265247 | 3/2009 |
| MX | 284569 B | 3/2011 |

* cited by examiner

METHOD FOR DISPLAYING TUMOR LOCATION WITHIN ENDOSCOPIC IMAGES

CROSS-REFERENCE TO RELATED APPLICATION

This application claims the benefit of and priority to U.S. Provisional Patent Application No. 62/798,854 filed Jan. 30, 2019, the entire disclosure of which is incorporated by reference herein.

BACKGROUND

Description of Related Art

As technology has advanced, surgeons have begun to replace classical open surgical techniques with minimally invasive techniques such as laparoscopic and thoracoscopic surgery in an effort to minimize trauma to surrounding tissue, reduce pain, reduce scarring, and reduce the length of time the patient is required to stay in the hospital. Minimally invasive surgery, such as the thoracoscopic approach pioneered in the mid-$19^{th}$ century, involves the use of small incisions (from one to several), typically no larger than 3-10 mm. Originally performed using a cystoscope, advances in medical technology lead to the development of specialized instruments for use in the thoracic cavity, such as a thoracoscope, to view the anatomy within the thoracic cavity while performing the surgical procedure. In the late $20^{th}$ century, Video Assisted Thoracic Surgery (VATS) was developed, which utilizes a fiber-optic endoscope to further reduce the size of the incisions required to perform the procedure and to provide clearer, more defined images of the thoracic cavity.

Concurrently, advances in medical imaging have enabled clinicians to more accurately depict the anatomy of a patient, and therefore, more accurately identify diseases and the location of any diseased tissue. These advances have enabled clinicians to more efficiently utilize minimally invasive surgical techniques, such as the thoracoscopic approach described above. Using medical imaging, such as CT (including X-ray CT, computerized axial tomography (CAT) scan, positron emission tomography (PET), and single-photon emission CT (SPECT)), a clinician is able to accurately identify lesions or other medical conditions without the need for invasive surgeries (such as an open approach or thoracotomy). However, due to the ability of modern imaging modalities to identify ever smaller lesions, which may be submucosal and not readily identified on images captured by a thoracoscopic (e.g., not visible on the thoracoscope image), surgeons must rely upon palpating tissue with their fingers to ascertain the precise location of the lesion within the tissue. As can be appreciated, palpating tissue with fingers during minimally invasive surgery is undesirable due to the need for additional ports through which the fingers of the surgeon can pass to enable the palpating of tissue.

To alleviate this issue, significant research and development has been focused on instruments enabling remote palpation, algorithms to identify the location of lesions within tissue, haptic feedback systems capable of notifying the surgeon when instruments are near a lesion, amongst others. However, such systems rely upon senses other than sight to identify the location of lesions in relation to surgical instruments.

SUMMARY

The disclosure is directed to a method of displaying an area of interest within a surgical site including modeling lungs of a patient, identifying a location of an area of interest within the model of the patient's lungs, determining a topography of a surface of the patient's lungs using a first camera, a light source, and a structured light pattern source associated with an endoscope, displaying, on a monitor associated with the endoscope, real-time images of the patient's lungs captured by a second camera associated with the endoscope, the second camera having a field of view, registering the real-time images of the patient's lungs with the model of the patient's lungs using the determined topography of the surface of the patient's lungs, and superimposing, over the real-time images of the patient's lungs, a marker indicative of the location of the area of interest within the patient's lungs, the marker remaining stationary within the patient's lungs as the field of view of the second camera changes.

In aspects, the method may include displaying, when the area of interest is outside of the field of view of the second camera, information indicative of the direction in which the area of interest is located relative to the field of view of the second camera.

In certain aspects, the method may include advancing the endoscope within a body cavity of a patient.

In other aspects, modeling the lungs of the patient may include acquiring computed tomography (CT) data of the patient's lungs.

In certain aspects, modeling the lungs of the patient may include acquiring tissue data of the patient's lungs.

In aspects, the method may include storing a software application within a memory associated with a computer, the computer having a processor configured to execute the software application, which when executed, creates a model of the patient's lungs based on the CT data and the tissue data.

In another aspect of the disclosure, a system for displaying an area of interest within a surgical site is provided including a computer having a processor configured to execute a software application, which when executed, creates a model of a patient's lungs and a monitor associated with the computer and an endoscope. The monitor is configured to display real-time images of the patient's lungs captured by a first camera associated with the endoscope having a field of view. The processor is configured to determine a topography of the patient's lungs, register the real-time images of the patient's lungs with the model of the patient's lungs using the determined topography of the surface of the patient's lungs, and superimpose, over the real-time images of the patient's lungs, a marker indicative of the location of the area of interest within the patient's lungs. The marker remains stationary within the patient's lungs as the field of view of the first camera changes.

In aspects, the computer may include a memory for storing computed tomography (CT) data and tissue data associated with the patient's lungs.

In certain aspects, the processor may be configured to display, when the area of interest is outside of the field of view of the first camera, information on the monitor indicative of the direction in which the area of interest is located relative to the field of view of the first camera.

In other aspects, the endoscope may be configured to be advanced within a body cavity of the patient.

In aspects, the processor may be configured to acquire computed tomography (CT) data of the patient's lungs.

In other aspects, the computer may be configured to acquire tissue data of the patient's lungs.

In certain aspects, the endoscope may include a second camera. In aspects, the endoscope may further include a light source. In other aspects, the endoscope may further include a structured light pattern source.

In other aspects, the topography of the patient's lungs may be determined using the second camera, the light source, and the structured light pattern source.

According to yet another aspect of the disclosure, a method of displaying an area of interest within a surgical site is provided including instructing a processor associated with a computer to execute a software application, which when executed, creates a model of a patient's lungs, displaying real-time images of the patient's lungs captured by a first camera associated with an endoscope on a monitor associated with the computer, the first camera having a field of view, and instructing to processor to determine a topography of the patient's lungs, register the real-time images of the patient's lungs with the model of the patient's lungs using the determined topography of the patient's lungs, and superimpose, over the real-time images of the patient's lungs, a marker indicative of the location of the area of interest within the patient's lungs, where the marker remains stationary within the patient's lungs as the field of view of the first camera changes.

In aspects, the method may include displaying, when the area of interest is outside the field of view of the first camera, information on the monitor indicative of the direction in which the area of interest is located relative to the field of view of the first camera.

In other aspects, determining the topography of the patient's lungs may include determining the topography of the patient's lungs using a second camera, a light source, and a structured light pattern source associated with the endoscope.

In certain aspects, instructing the processor associated with the computer to execute the software application may include acquiring computed cosmography (CT) data and tissue date of the patient's lungs.

BRIEF DESCRIPTION OF THE DRAWINGS

Various aspects and features of the disclosure are described hereinbelow with reference to the drawings, wherein.

DETAILED DESCRIPTION

Figure 1:
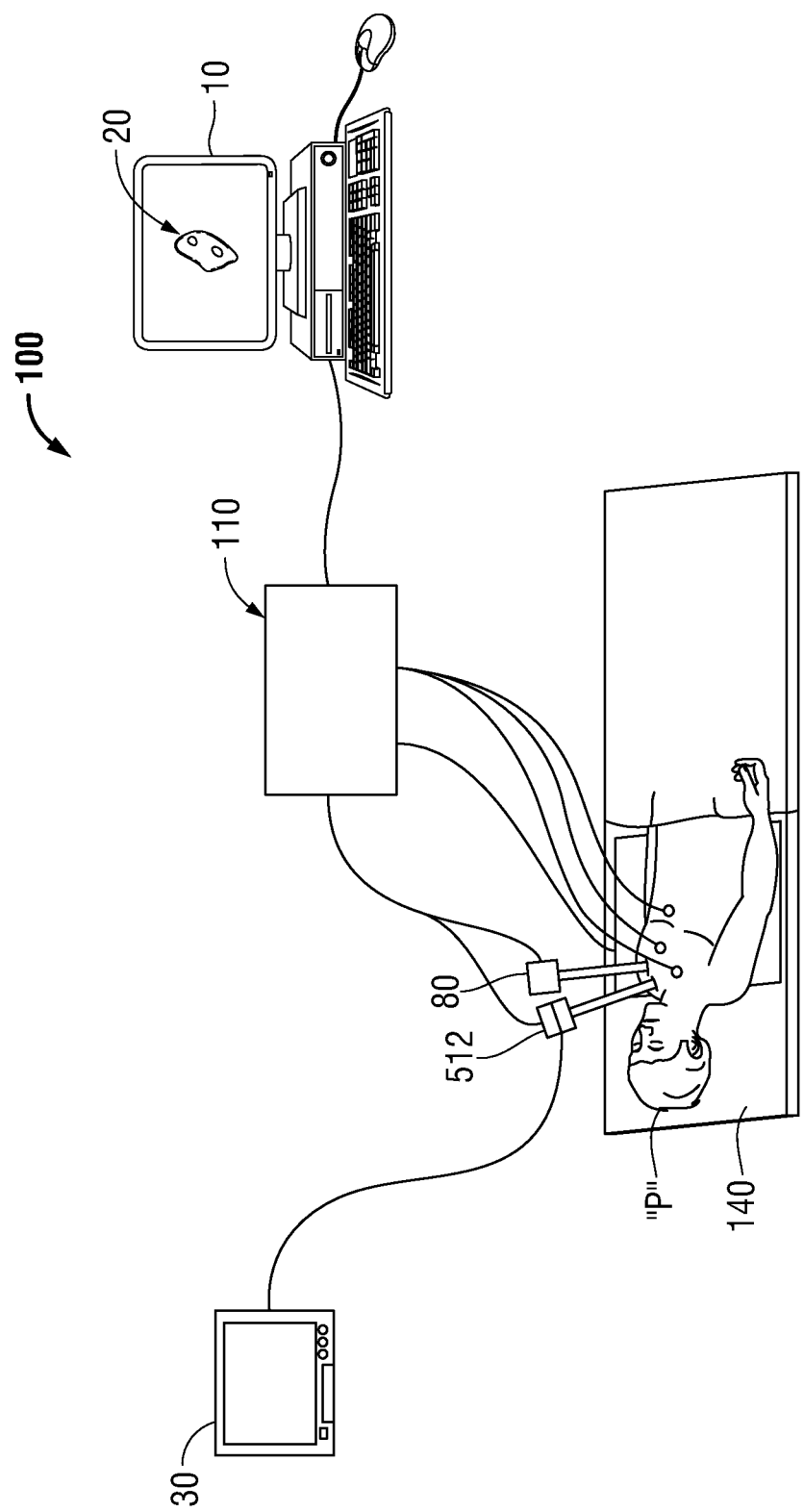
FIG. 1 is a perspective view of a system provided in accordance with the disclosure configured for modeling a lung and treating an area of interest within the lung.

The disclosure is directed to methods and systems for displaying a location of an area of interest within a surgical site. As described herein, a three-dimensional (3D) model of the patient's lungs is generated using previously obtained computed tomography (CT) data of the patient's lungs. The patient is imaged using any suitable CT device and the data is stored within a memory associated with a computer. A software application that is stored within the memory is executed by the computer to enable a clinician to review the image data. By reviewing the image data, the clinician is able to identify an area of interest indicative of lung disease and determine its location within the lungs of the patient. Once the area of interest and its location is identified by the clinician, the software application processes the image data and generates a 3D reconstruction or model of the CT images. As can be appreciated, during a thoracoscopic procedure, it is necessary to deflate a portion of the patient's lungs in order to provide the requisite space within the thoracic cavity for the surgical tools to be maneuvered. The software application is able to model the patient's lungs in a collapsed state using a segmentation algorithm to define the boundaries of various types of tissue and grouping together similar types of tissue based on their density, continuity, etc. In this manner, the accuracy of the 3D reconstruction of the patient's lungs is enhanced, enabling the clinician to develop a more accurate preoperative plan than is ordinarily possible using standard techniques.

When beginning the surgical procedure, the clinician penetrates the patient's chest using a trocar or any other suitable access device and advances a surgical instrument, such as forceps, a surgical stapler, or the like, in addition to a second surgical tool, such as a thoracoscope, to capture real-time images of the patient's anatomy during the surgical procedure. The thoracoscope includes a structured light scanner capable of scanning a pattern on the patient's anatomy within the thoracic cavity. In addition, the thoracoscope includes an infrared (IR) camera capable of detecting IR light to detect the pattern scanned onto the patient's anatomy by the structured light scanner. Using the information gathered by the thoracoscope, the software application generates a 3D surface model of the patient's collapsed lung. In this manner, the software application is able to update the collapsed lung model and provide a more accurate model of the patient's lungs in the collapsed state. It is contemplated that the software application can display various generated 3D models of the patient's lungs to the clinician and enable the clinician to select the model that most accurately depicts the patient's lungs in the collapsed state. Additionally, rather than comparing the 3D model of the lungs to the scan obtained by the structured light scanner, it is contemplated that the 3D model may be compared to the clinician's real-time view obtained by the thoracoscope.

Using positional data obtained by the IR camera, various feature points or fiducials are detected within the structured light scanner data, such as fissures, ligament attachments, adhesions, etc. Using this data, the 3D model can be correlated to, or registered with, the real-time view of the patient's lungs in the collapsed state. In this manner, the area of interest and other structures can be superimposed over the real-time view of the patient's lungs to enable the clinician to more accurately treat the area of interest and avoid critical structures located within the patient's lungs. The area of interest may be represented by a marker, such as a red dot, that is superimposed on the real-time view of the patient's lungs such that the clinician may continuously observe the location of the area of interest while navigating the surgical instrument within the body cavity and within the patient's lungs. In embodiments, the marker may be superimposed within the patient's lungs, rather than on its surface, to more accurately depict the location of the area of interest within the patient's lungs.

As the clinician manipulates the thoracoscope relative to the area of interest, the marker remains located at the area of interest. In this manner, as the thoracoscope is manipulated and the field of view of the camera associated with the thoracoscope changes, the marker remains stationary within the patient's lungs. However, should the clinician manipulate the thoracoscope such that the area of interest is no longer within the field of view of the camera, the software application superimposes an arrow or other indicator over the real-time view of the patient's lungs indicative of the direction in which the area of interest is located relative to the field of view of the camera. As can be appreciated, the arrow may be superimposed at right, left, in, out, up, down locations within the real-time view of the patient's lungs.

Although the systems and methods detailed herein are generally described with respect to the lungs, it is contemplated that the following systems and methods may be applied to the liver, spleen, or any other organ.

Embodiments of the disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. Although generally described herein as the various determination and/or selection steps being performed by a clinician, it is contemplated that the determination and/or selection steps described herein may be performed by the software application, or a combination of clinician and software application input. As can be appreciated, in certain instances, it may be necessary for the software application to make certain determinations, whereas in other instances it may be necessary for the clinician to make certain determinations. In embodiments, the software application may make a determination and present the determination to the clinician for selection and/or confirmation. In other embodiments, it may be necessary for the software application to provide a prompt or other warning to the clinician regarding the consequences of the clinician's decision, or to provide an alternative selection to the clinician, or combinations thereof. In the following description, well-known functions or constructions are not described in detail to avoid obscuring the disclosure in unnecessary detail.

As illustrated in FIG. 1, the methods described hereinbelow utilize a system 100 including a navigation system capable of guiding a surgical tool 80 within the thoracic cavity and the patient's "P" lungs "L" to an area of interest "AOI." The navigation system includes a tracking system 110 that is configured for use with the surgical tool 80 and enables monitoring of the position and orientation of a distal portion of the surgical tool 80. The system 100 further includes a computer 10 and a user interface 20 displayed on a display associated with the computer 10 or suitable monitoring equipment 30 (e.g., a video display). The role and use of the system 100 with the methods described herein will be described in further detail hereinbelow.

Figure 2:
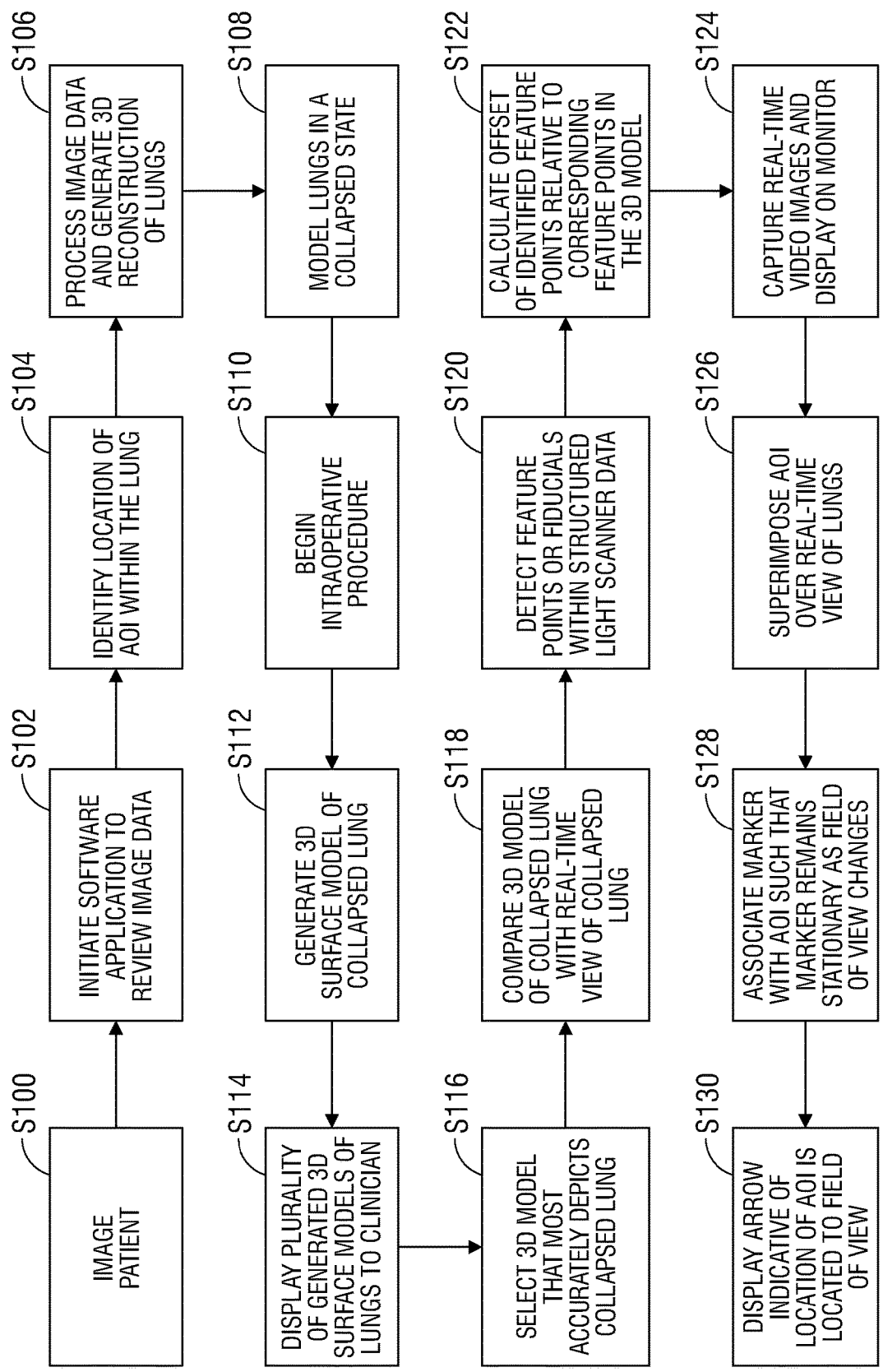
FIG. 2 is a flow chart showing a method of modeling a lung and performing a surgical procedure according to the disclosure.

With reference to the flow chart depicted in FIG. 2, a method of treating a patient using a generated model of the lungs "L" of a patient "P" using computed tomography (CT) data is described. Initially, in step S100, the patient "P" is imaged using any suitable CT device (not shown), such as X-ray CT, computerized axial tomography (CAT) scan, positron emission tomography (PET), and single-photon emission CT (SPECT), and the imaging data is stored within a memory (not shown) coupled to the computer 10 (FIG. 1). The memory may include any non-transitory computer-readable storage media for storing data and/or software that is executable by a processor (not shown), e.g., solid-state, volatile, non-volatile, removable, and non-removable. As can be appreciated, the images may be stored within a memory associated with a remote computer or network (not shown) such as a distributed network or the internet via a wired or wireless connection for the transmission and reception of data to and from other sources. It is further contemplated that the images may be stored on one or more removable storage devices (not shown), such as optical disks, memory cards, Zip disks or Floppy Disks, Disk packs, Magnetic tapes, USB flash drives, external hard drives, amongst others.

Following imaging of the patient, in step S102, a software application stored within the memory is executed by a processor associated with the computer to enable review of the image data. One example of such an application is ILOGIC® planning and navigation suites currently marketed by Medtronic PLC. An area of interest ("AOI;" FIG. 5) illustrating the effects of lung disease (e.g., emphysema, COPD, asthma, cancer, or the like) is identified in the images and its location determined within the lungs "L" of the patient "P." Several imaging methods used for identifying an area of interest "AOI" are contemplated such as ultrasound, CT scan, metabolic scanning, amongst others. In one non-limiting embodiment, hypodense portions of the lungs "L" may be identified in the CT images which correlate to areas affected by emphysema as the expanded floppy alveoli of bulla will provide images which may be substantially darker or blacker than the surrounding tissue. In certain embodiments, a device capable of performing a combined PET/CT imaging technique may be utilized to identify hypodense areas of the lungs "L." After analysis of the image data, using one of the above-described techniques, in step S104, the location of the area of interest "AOI" within the lung "L" may be identified and its location stored within the memory coupled to the computer 10 (FIG. 1).

Figure 3A:
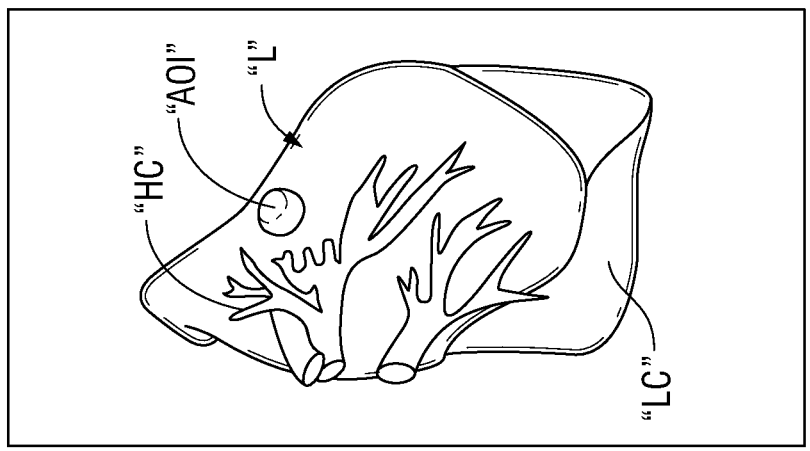
FIG. 3A is a cross-sectional view of a 3-D model of the patient's lung showing an area of interest and high contrast "HC" and low contrast "LC" density details.

Referring to FIG. 3A, in conjunction with FIG. 2, in step S106, the image data obtained during step S100 is processed by the software application and a 3D reconstruction of the CT images is generated using any suitable method known in the art. As can be appreciated, during a thoracoscopic procedure such as that described hereinbelow, it is necessary to deflate a portion of the patient's lungs (e.g., induce atelectasis) in order to provide the requisite space within the thoracic cavity for the surgical tools to be maneuvered. As described hereinabove, the 3D reconstruction is necessarily a reconstruction of a fully inflated lung. Therefore, once the surgical procedure has begun, the geometry of the lungs changes leading to a shift in the location of the identified area of interest "AOI" within the lungs and thoracic cavity. Thus, the pre-operative plan that is developed as described in detail hereinbelow must compensate for the altered geometry of the lung during the surgical procedure.

Figure 3B:
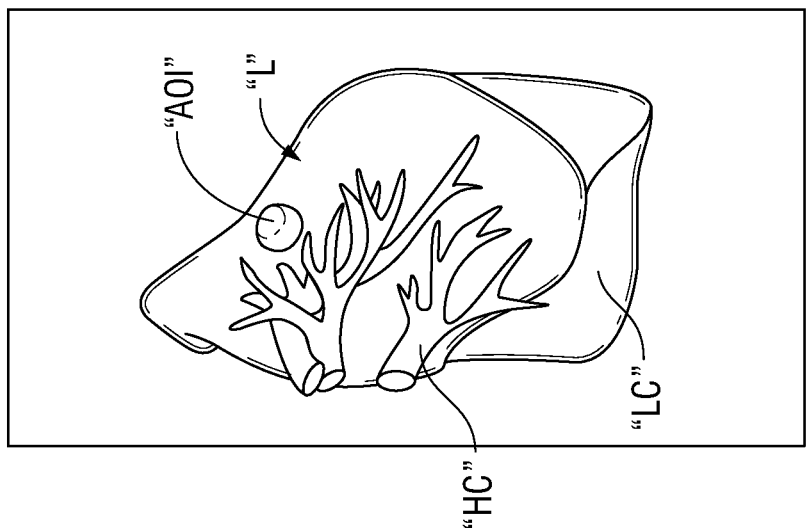
FIG. 3B is a cross-sectional view of a 3-D model of the patient's lungs showing high contrast "HC" and low contrast "LC" density details that have been differentiated and grouped together.

To compensate for this altered geometry, in step S108, the software application models the patient's "P" lung "L" in a collapsed state. Specifically, the software application employs a segmentation algorithm to define the boundaries of various types of tissues and group together similar types of tissue based on their density and continuity, amongst other factors (FIG. 3B). It is contemplated that the software application may utilize any suitable segmentation algorithm, such as binary masking, determination of the optimum threshold that separates tissue and background, adaptive region growing, wavefront propagation, or the like.

Figure 3C:
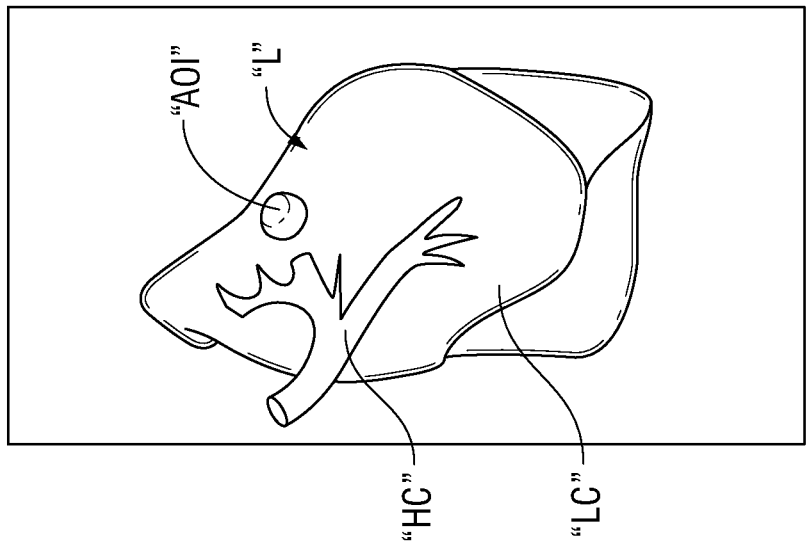
FIG. 3C is a cross-sectional view of a 3-D model of the patient's lungs showing high contrast "HC" and low contrast "LC" density details that have been partially differentiated.

As can be appreciated, the software application may not be able to differentiate all of the differing tissue types (FIG. 3C). As such, the software application enables selective toggling of arteries, veins, bronchi, and the like to correct any inaccuracies. In this manner, the software application presents each segmented group as a different color or different transparency level that may be selectively adjusted by the clinician in order to enable the clinician to better identify each segmented or differentiated group, or in embodiments, may present identified structures as opaque and unidentified structures as translucent, or vice versa.

Figure 4:
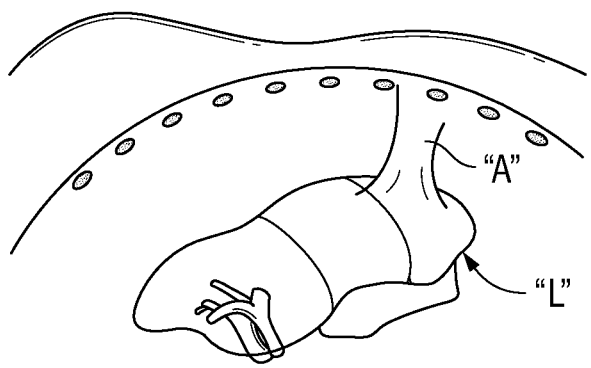
FIG. 4 is a cross-sectional view of a 3-D model of the patient's thoracic cavity showing the lungs and adhesions attached thereto.

To further enhance the accuracy of the reconstruction of the collapsed lung, the software application adjusts the 3D reconstruction to account for the effect of gravity (e.g., the orientation of the patient on the operating table 140) and the curvature of the patient's spine in the coronal or frontal plane (e.g., the plane dividing the patient's "P" body into ventral and dorsal sections). Other structures within the thoracic cavity affect lung volume and placement of the lungs within the patient's thoracic cavity, such as adhesions "A", lesion, of the like (FIG. 4). The software application recognizes such structures via the previously obtained images of the patient's "P" lungs "L" and accounts for the presence of these structures by forcing the lung "L" to sit higher in the thoracic cavity, in the case of the presence of an adhesion "A", by fixing the adhesions "A" to a fixed boundary at the ribcage and applying elastic models to determine displacement, or combinations thereof. In the alternative, the software application may recognize the removal of adhesions, or removal of the adhesions may be manually entered into the synthesizer by the clinician, and the software application will readjust the model accordingly (e.g., the lung "L" will sit further down towards the hilum.

Figure 5:
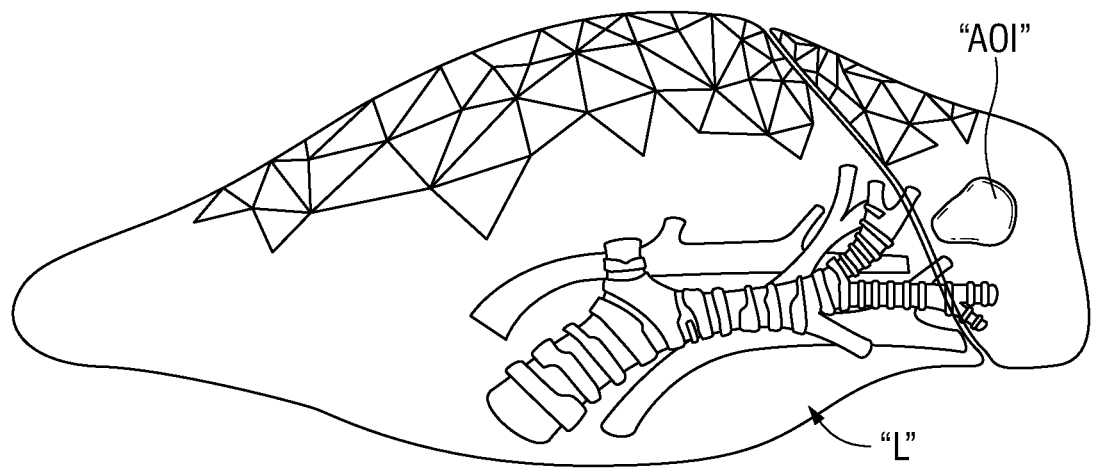
FIG. 5 is a cross-sectional view of a 3-D model of the patient's lungs showing the model having a generated mesh applied thereto.
Figure 6:
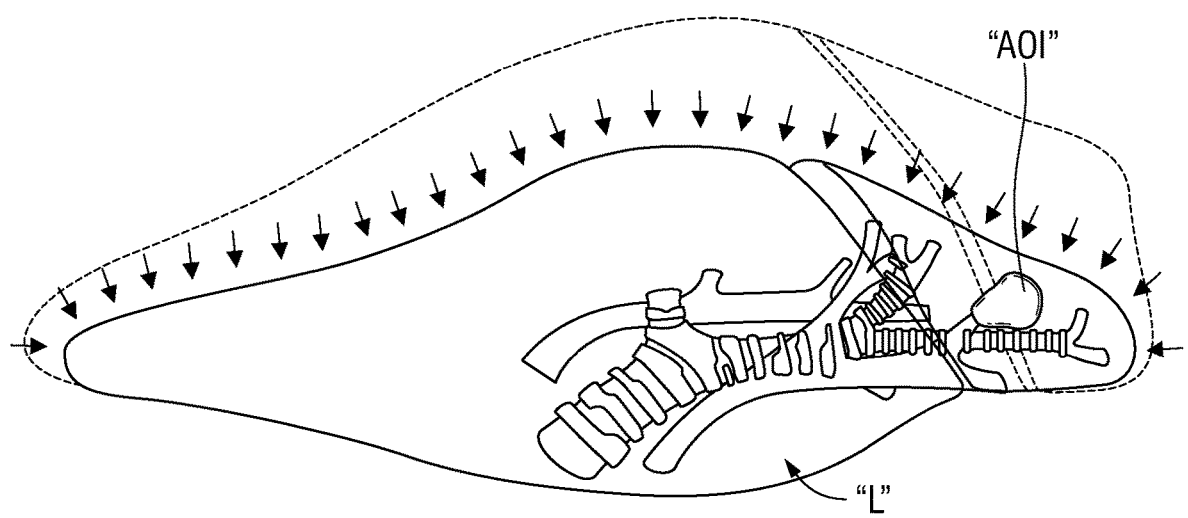
FIG. 6 is a cross-sectional view of a 3-D model of the patient's lungs showing the lungs in a collapsed state.

It is envisioned that the software application can estimate a more likely level of lung deflation as the elastic properties of the lung tissues will be affected by common lung conditions such as COPD, the age of the patient, smoking status of the patient, etc. Additionally, the software application can take into account prior surgical procedures the patient "P" may have undergone that would impact overall lung volume. After identifying the various structures within the lung "L," the software application employs a Finite Element Analysis (FEA) algorithm to model the lung "L" and present the collapsed lung model to the clinician on the display 20 (FIGS. 5 and 6). The resulting 3D model of the collapsed lung forms a Computational Lung Model (CLM) that is the 3D model that is displayed to the clinician on the display 20 or monitoring equipment associated with the computer 110 during pre-operative planning, intra-operative assistance, and post-operative review.

Figure 7:
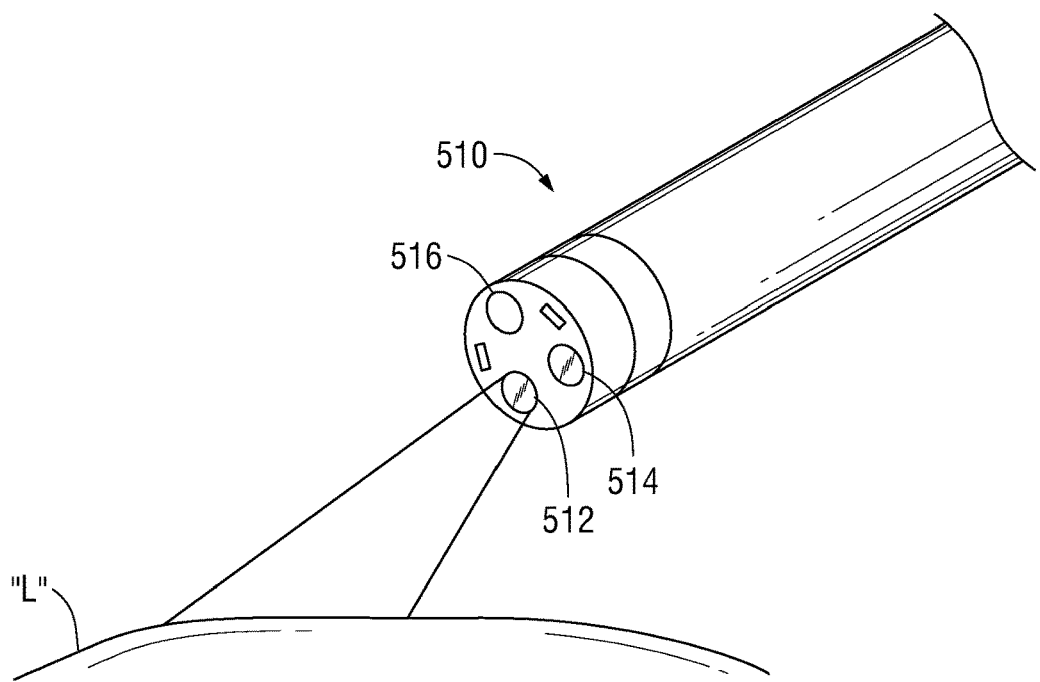
FIG. 7 is a perspective view of a thoracoscope provided in accordance with the disclosure having a structured light scanner disposed thereon.
Figure 8:
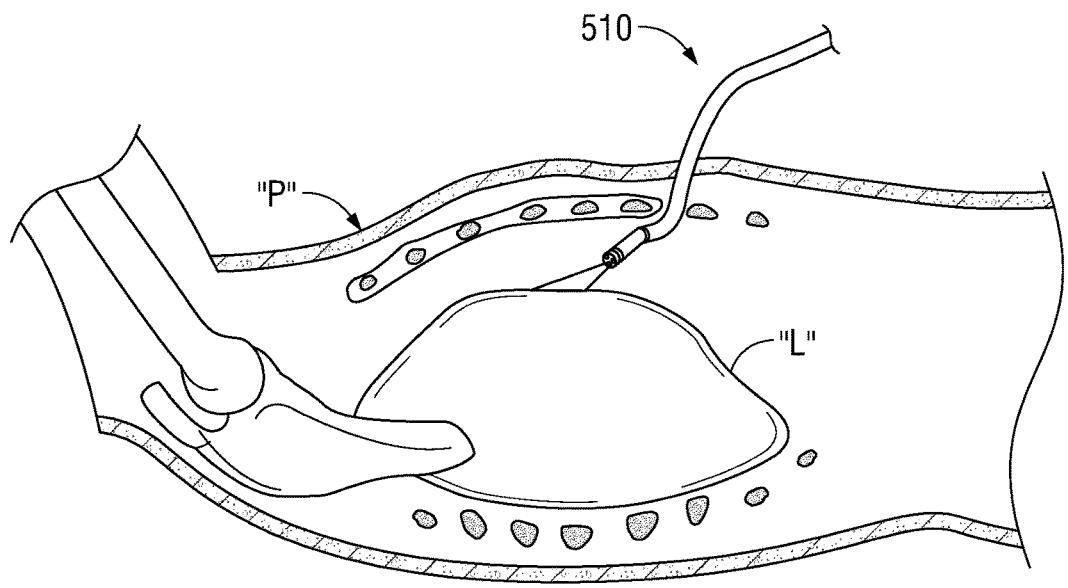
FIG. 8 is a side, cross-sectional view of the patient's thoracic cavity showing the thoracoscope of FIG. 7 advanced therein.

With reference to FIGS. 7 and 8, after the CLM has been developed, in step S110, the clinician may begin the desired procedure by penetrating the patient's "P" chest using a trocar (not shown) or other suitable access device through which a surgical instrument 400 (e.g., forceps, surgical stapler, electrosurgical instrument, clip applier, or the like) is advanced into the patient's "P" body cavity. As can be appreciated, a second surgical tool is advanced within the body cavity of the patient "P" to capture real-time images of the patient's anatomy during the surgical procedure. In one non-limiting embodiment, the second surgical tool is a thoracoscope 510 or other suitable device, such as an endoscope or laparoscope, capable of being advanced within the thoracic cavity of a patient "P" and having a structured light scanner 512 (FIG. 7) disposed thereon. It is contemplated that the thoracoscope 510 may include any suitable structured light scanner 512 known in the art, such as a light emitting diode "LED" or LED infrared laser, or a visible light LED laser, that is disposed in a suitable manner on the thoracoscope 510 to scan a pattern (e.g., line, mesh, dots, etc.), by a rotating mirror, a beam splitter, or diffraction grating, or may be a digital light processing (DLP) projector. In one non-limiting embodiment, the structured light scanner 512 is an LED laser having collimated light. The thoracoscope 510 further includes an IR camera 514 (FIG. 7) disposed thereon that is capable of detecting IR light. It is contemplated that the IR camera 514 may be any thermographic camera known in the art, such as ferroelectric, silicon microbolometer, uncooled focal plane array (UFPA), amongst others. It is further contemplated that the various sensors disposed on the thoracoscope 510 may be separate and distinct components with associated hardware and/or software, or may be part of a commercial platform such as Intel®'s RealSense™. The thoracoscope 510 is a steerable thoracoscope capable of being manipulated relative to a longitudinal axis defined through proximal and distal portions of the thoracoscope 510, such that a distal portion of the thoracoscope 510 can be oriented at various angles relative to the patient's "P" lungs "L" (FIG. 8). As can be appreciated, a steerable thoracoscope is capable of capturing the required images of the patient's "P" lungs "L" without being removed from the patient's "P" body cavity. In contrast, if the thoracoscope 510 is a rigid thoracoscope, it may be necessary to advance the rigid thoracoscope through multiple incisions or trocars in order to take the necessary images of the patient's "P" lungs "L" to generate the 3D surface model of the patient's "P" lungs "L."

Figure 9A:
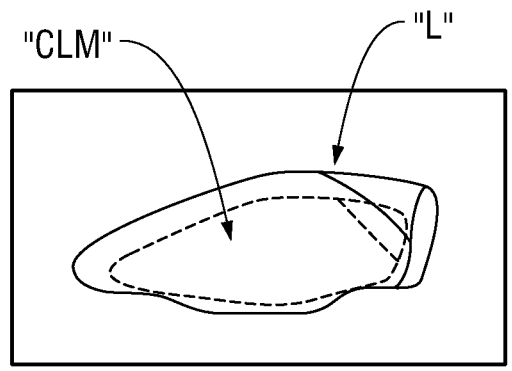
FIG. 9A is an illustration of the user interface of the system of FIG. 1, displaying the patient's lung in a collapsed state, with a 3D model of the collapsed lung overlaid thereon.
Figure 9B:
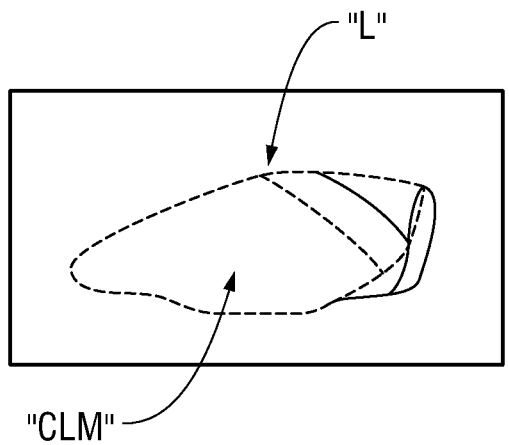
FIG. 9B is an illustration of the user interface of the system of FIG. 1, displaying the patient's lung in a collapsed state, with another 3D model of the collapsed lung overlaid thereon.
Figure 9C:
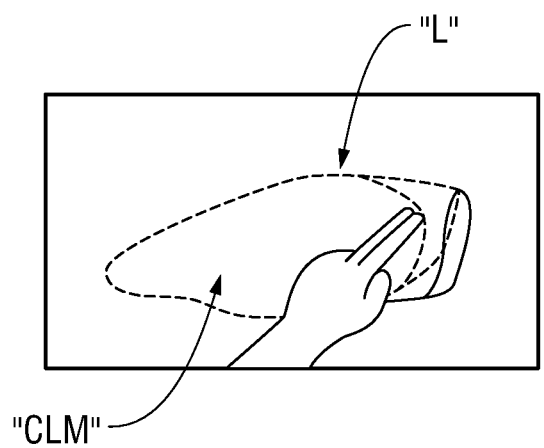
FIG. 9C is an illustration of the user interface of the system of FIG. 1, displaying the patient's lung in a collapsed state, with yet another 3D model of the collapsed lung overlaid thereon.

Using the information gathered by the thoracoscope 510, in step S112, the software application generates a 3D surface model of the patient's "P" collapsed lung "L." The 3D surface model of the collapsed lung is utilized by the software application to update the CLM and provide a more accurate model of the patient's "P" lungs "L" in the collapsed state. In step S114 (FIGS. 9A-9C), the software application displays a plurality of generated 3D surface models of the patient's lungs to the clinician via the user interface 20. In step S116, the software application enables the clinician to select a lung deflation model that most accurately depicts the patient's "P" lung "L" in the collapsed state (FIGS. 9A-9C). For example, FIG. 9A illustrates the CLM superimposed over the scan of the patient's lung in the collapsed state. FIG. 9B illustrates a selected CLM that most accurately matches the scan of the patient's lung in the collapsed state. FIG. 9C illustrates the clinician using hand gestures to alter the shape and rotation of the CLM to more closely match the scan of the patient's lung in the collapsed state. In embodiments, the clinician may alter the shape and rotation of the CLM in real-time. In this manner, the clinician may adjust, in real-time, the amount of inflation or deflation of the lung, adjusting the amount of rotation of the lung in the thoracic cavity in each of the X, Y, and Z axes, etc.

Figure 10:
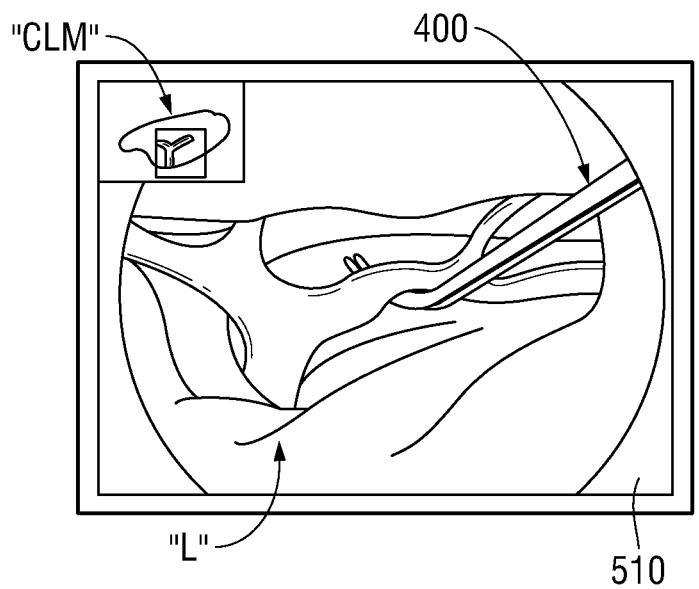
FIG. 10 is an illustration of the user interface of the system of FIG. 1, showing a camera view from the thoracoscope of FIG. 7.

With reference to FIG. 10, it is further contemplated that, rather than comparing the CLM to the scan obtained by the structured light scanner 512, in step S118, the CLM may be compared to the clinician's real-time view of the patient's "P" collapsed lung "L" obtained by the thoracoscope 510. In this manner, the thoracoscope 510 includes a camera 516 or other suitable device for capturing video images disposed at a distal portion thereof. As can be appreciated, the thoracoscope 510 may be any suitable thoracoscope capable of being used during a video-assisted thoracoscopic surgical (VATS) procedure, image-guided video-assisted thoracoscopic surgical (iVATS) procedure, or robotic-assisted thoracoscopic surgical (RATS) procedure. In embodiments, the camera 516 may be an optical scanning system (not shown), such as a digital light processing (DLP) system, that may be utilized to accurately size the patient's "P" lung "L" in the collapsed state.

Figure 11:
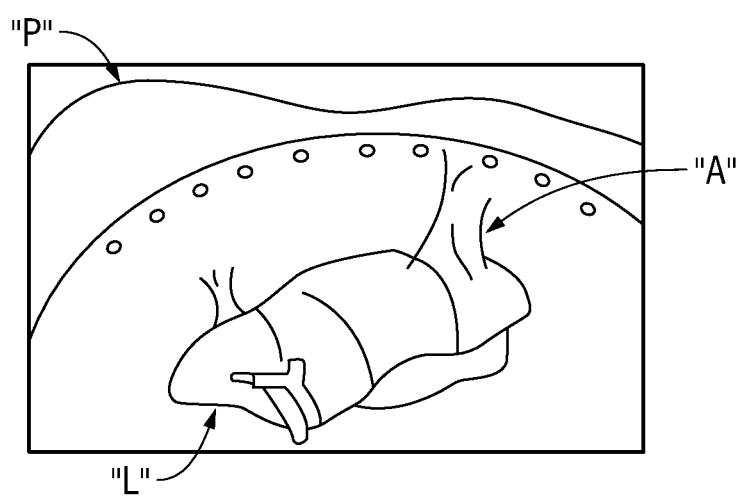
FIG. 11 is an illustration of the user interface of the system of FIG. 1, displaying a cross-sectional view of a 3D model of the patient's thoracic cavity showing the lungs and adhesions attached thereto.

In step S120, using positional data obtained by the IR camera 514, or the optical scanning system, various feature points or fiducials are detected within the structured light scanner data, such as fissures, ligament attachments, adhesions "A," the surface height of the patient's "P" lungs "L," or any other suitable feature point located within the thoracic cavity (FIG. 11). Once the feature points are identified, in step S122, the offset of these detected feature points relative to corresponding feature points in the collapsed CLM is calculated. It is contemplated that the offset of the feature points between the structured light scanner data and the CLM data may be calculated using any suitable feature matching algorithm, such as Scale-Invariant Feature Transform (SIFT), Rotation-Invariant Feature Transform (RIFT), Generalized Robust Invariant Feature (G-RIF), Speeded Up Robust Features (SURF), Principal Component Analysis SIFT (PCA-SIFT), Gradient Location-Orientation Histogram (GLOH), Gauss-SIFT, or the like. The software application uses the calculated offsets of the feature points and regenerates the CLM to more accurately reflect the observed condition of the patient's "P" collapsed lung "L." As can be appreciated, the CLM can be regenerated in real time as the thoracoscope 510 is advanced within the thoracic cavity relative to the patient's "P" lung "L." In this manner, the software application of the synthesizer 300 monitors the location of visual landmarks, such as fissures, lesions, or the like, or may use internal landmarks such as nodules (identifiable through the use of lesion detection technology) or fiducials (not shown) that have been previously placed within the patient's "P" lung "L." In embodiments, the software application may detect a lesion within the patient's "P" lung "L" and treat the lesion as a natural fiducial, such that critical structures within the patient's "P" lung "L" can be identified within the CLM.

Figure 12:
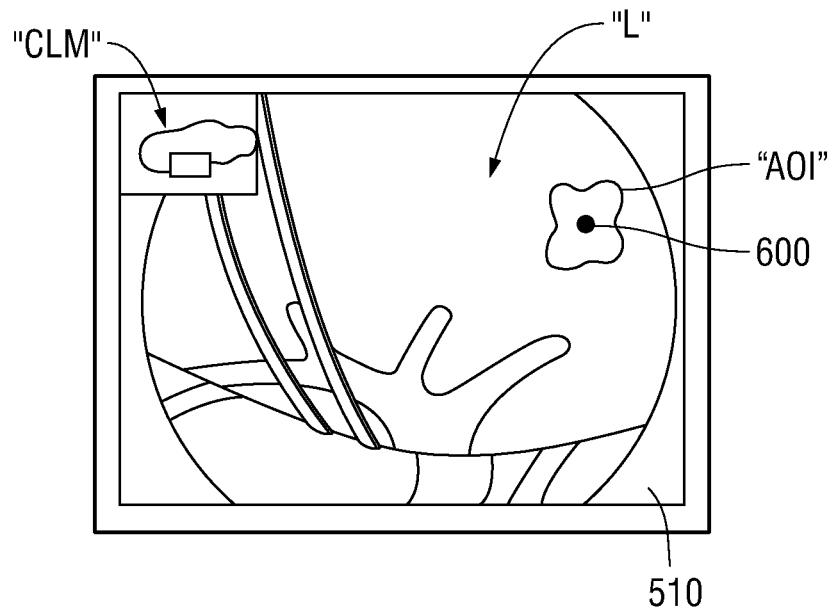
FIG. 12 is an illustration of the user interface of the system of FIG. 1, showing a real-time view of the patient's lungs captured by the thoracoscope of FIG. 7 and illustrating an area of interest indicated by a marker superimposed over the real-time view of the patient's lungs.

As the thoracoscope 510 is advanced within the thoracic cavity, in step S124, video images are captured and transmitted to the monitor associated with the computer 10 or the monitoring equipment 30 (FIG. 1), providing a real time view of the patient's "P" collapsed lung "L." After correlating or registering the CLM to the real-time view of the patient's "P" collapsed lung "L" obtained by the thoracoscope 510, the area of interest "AOI" and other structures inside the lung "L" are superimposed over the real-time view of the patient's "P" lungs "L" in step S126 to enable the clinician to more accurately treat the area of interest "AOI" and avoid critical structures located within the lung "L" (FIG. 12). In embodiments, the area of interest "AOI" may be represented by a marker 600 (FIG. 12), such as a red dot, that is superimposed on the real-time view of the patient's "P" lungs "L" such that the clinician may continuously observe the location of the area of interest "AOI" while navigating the surgical instrument 400 within the body cavity and within the patient's "P" lung "L." It is envisioned that the marker 600 may be superimposed within the patient's "P" lungs "L," rather than on the surface of the patient's "P" lungs "L" to more accurately depict the location of the area of interest "AOI" within the patient's "P" lungs "L."

Figure 13:
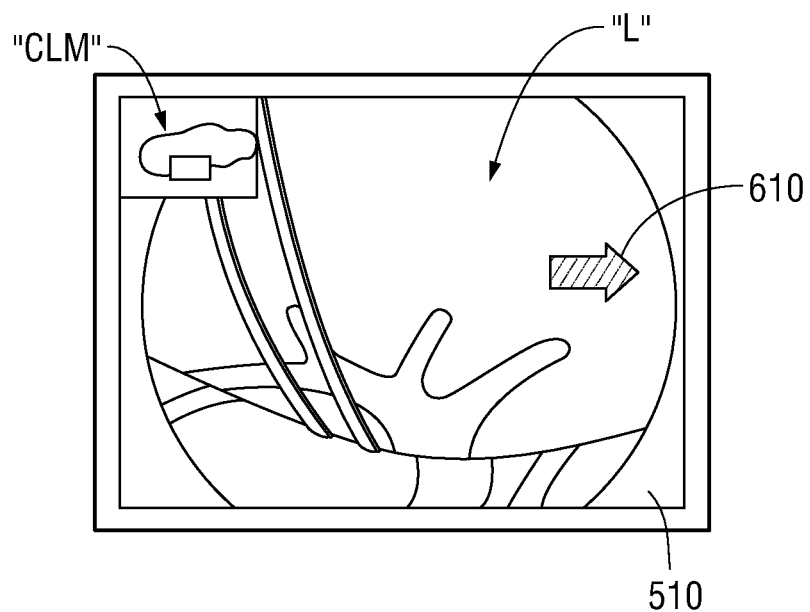
FIG. 13 is an illustration of the user interface of the system of FIG. 1, showing a real-time view of the patient's lungs captured by the thoracoscope of FIG. 7 and illustrating an arrow superimposed over the real-time view of the patient's lungs indicating the direction in which the area of interest is located relative to the field of view of the thoracoscope.

In step S128, it is contemplated that as the clinician manipulates the thoracoscope 510 relative to the area of interest "AOI," the marker 600 remains located at the area of interest "AOI." In this manner, as the thoracoscope 510 is manipulated and the field of view of the camera 516 of the thoracoscope 510 changes, the marker 600 remains stationary within the patient's "P" lungs "L." However, should the clinician manipulate the thoracoscope 510 such that the area of interest "AOI" is no longer within the field of view of the camera 516 of the thoracoscope, in step S130, the software application superimposes an arrow 610 or other indicator over the real-time view of the lungs "L" indicative of the direction in which the area of interest "AOI" is located relative to the field of view of the camera 516 of the thoracoscope (FIG. 13). As can be appreciated, the arrow

610 can be superimposed at right, left, in, out, up, down locations within the real-time view of the lungs "L."

Figure 14:
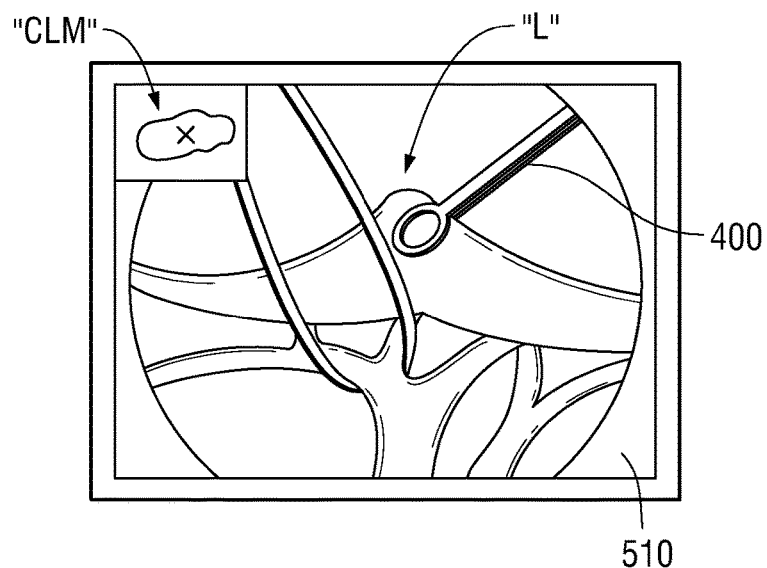
FIG. 14 is an illustration of the user interface of the system of FIG. 1, showing the camera view from the thoracoscope of FIG. 7 with the clinician manipulating the patient's lung.

It is further contemplated that the CLM can reflect manipulation of the lungs "L" by the clinician. As illustrated in FIG. 14, as the clinician manipulates a portion of the lungs "L" using any suitable surgical instrument 90, such as surgical forceps or the like, the CLM may be updated to reflect the current position of the lungs "L" within the thoracic cavity. In this manner, the location of the structures within the lungs "L" and the area of interest "AOI," and in particular, the marker 600 (FIG. 12) representing the area of interest "AOI," may be updated to reflect their true location based upon how the lungs "L" have been manipulated by the clinician.

Surgical instruments such as the endoscopes, computing devices, and other components of system 100 described herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely controls the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, endoscopes, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

It is contemplated that the systems described herein may be positioned by the robotic system and the precise position of the endoscope transmitted to the computer to construct the 3D image of the scanned organ or operative field. The robotic system has the ability to autonomously scan the surgical field and construct a complete 3D model of the field to aid the surgeon in directing the robotic arms or to provide necessary 3D information for the robotic system to further conduct surgical steps autonomously. In embodiments, where the endoscope includes a camera and a structured light source that are independent of one another, the robotic system may direct the camera and a structured light source separately. The robotic system provides the relative coordinates between respective endoscopes needed to triangulate the points in the structured light and camera views to construct a 3D surface of the operative field. In this manner, the robotic system has a specific advantage of being able to autonomously position the structure light source onto the field of view of the camera or camera endoscope. Additionally, or alternatively, with the robot controlling the camera location (or other component location), the robot may move the camera (or other component) to expand the size of the scanned anatomy (e.g., the amount scanned) to create a larger view for the user (e.g., surgeon) without input or knowledge by the user.

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 15:
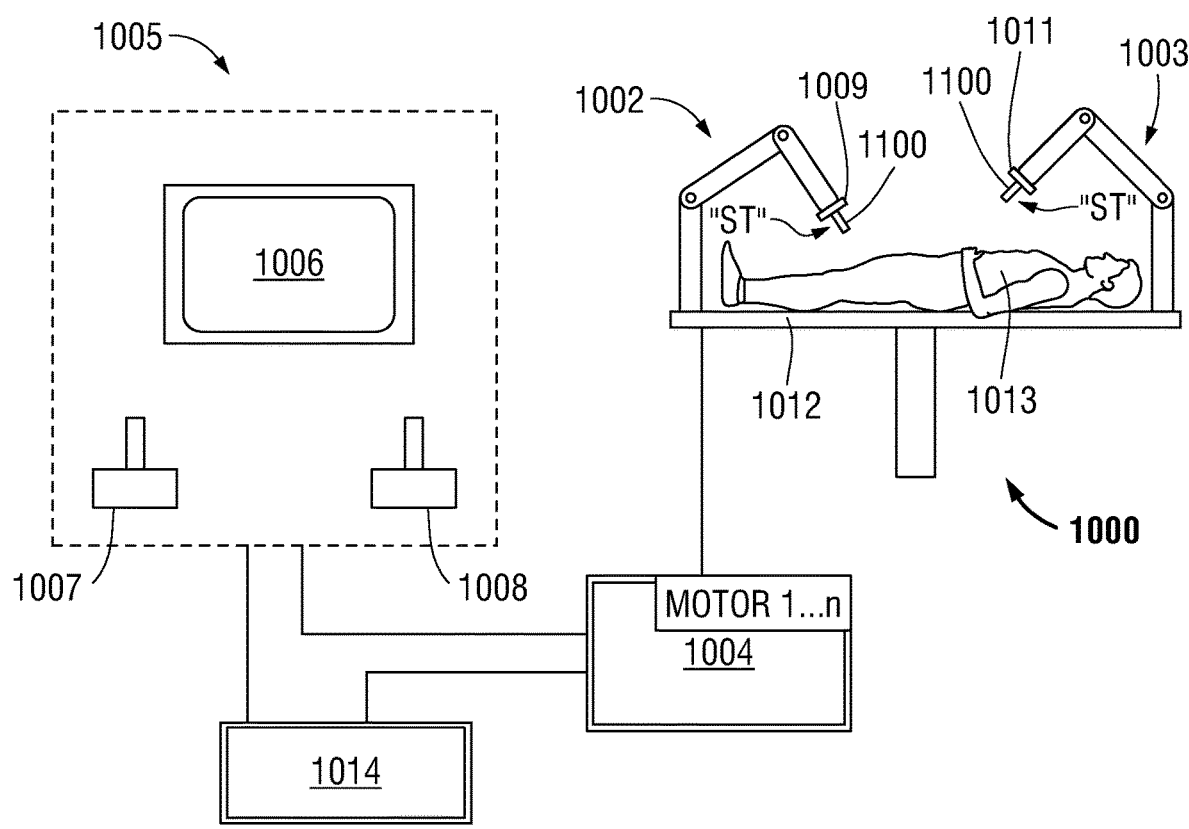
FIG. 15 is a schematic illustration of a robotic surgical system configured for use in accordance with the disclosure.

Referring to FIG. 15, a medical work station is shown generally as work station 1000 and generally may include a plurality of robot arms 1002, 1003; a control device 1004; and an operating console 1005 coupled with control device 1004, Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1020, in accordance with any one of several embodiments disclosed herein.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient "P" lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being "P" and/or anatomical atlases.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments.

What is claimed is:

1. A method of displaying an area of interest within a surgical site, comprising:
   generating a three-dimensional (3D) model of lungs of a patient from preoperative images;
   identifying a location of an area of interest within the preoperative images;
   generating collapsed state 3D models of the patient's lungs in a collapsed state;
   updating the location of the area of interest in the collapsed state 3D models;
   depicting the area of interest within at least one of the collapsed state the 3D models model of the patient's lungs;
   determining a topography of a surface of the patients lungs using a first camera, a light source, and a structured light pattern source of an endoscope;
   displaying, on a monitor associated with the endoscope, real-time images of the patients lungs captured by a second camera of the endoscope, the second camera having a field of view;
   registering the real-time images of the patient's lungs with the at least one collapsed state 3D model of the patients lungs using the determined topography of the surface of the patient's lungs; and
   superimposing, over the real-time images of the patient's lungs, a marker indicative of the location of the area of interest within the at least one collapsed state 3D model of the patient's lungs, a displayed position of the marker remaining stationary relative to the displayed real-time images of the patient's lungs as the field of view of the second camera changes.

2. The method according to claim 1, further comprising displaying, when the area of interest is outside of the field of view of the second camera, information indicative of a direction in which the area of interest is located relative to the field of view of the second camera.

3. The method according to claim 1, further comprising advancing the endoscope within a body cavity of the patient.

4. The method according to claim 1, wherein generating the 3D model of the lungs of the patient includes acquiring computed tomography (CT) data of the patient's lungs.

5. The method according to claim 4, wherein generating & the collapsed state 3D models of the lungs of the patient includes acquiring tissue data of the patient's lungs.

6. The method according to claim 5, further comprising storing a software application within a memory of a computer, the computer having a processor configured to execute the software application, which when executed, creates the collapsed state 3D models of the patient's lungs based on the CT data and the tissue data.

7. A system for displaying an area of interest within a surgical site, comprising:
   a computer having a processor configured to execute a software application, which when executed, creates a three-dimensional (3D) model of a patient's lungs from preoperative images; and
   a monitor associated with the computer and connected to an endoscope, the monitor configured to display real-time images of the patients lungs captured by a first camera of the endoscope, the first camera having a field of view,
   wherein the processor is configured to determine a topography of the patient's lungs, generate a collapsed state 3D model, register the real-time images of the patients lungs with the collapsed state 3D model of the patients lungs using the determined topography of the a surface of the patient's lungs, and superimpose, over the real-time images of the patients lungs, a marker indicative of the a location of the area of interest within the patients lungs as the area of interest appears in the collapsed state 3D model, a displayed position of the marker remaining stationary relative to the displayed real-time images of the patients lungs as the field of view of the first camera changes.

8. The system according to claim 7, wherein the computer includes a memory for storing computed tomography (CT) data and tissue data associated with the patient's lungs.

9. The system according to claim 7, wherein the processor is configured to display, when the area of interest is outside of the field of view of the first camera, information on the monitor indicative of a direction in which the area of interest is located relative to the field of view of the first camera.

10. The system according to claim 7, wherein the endoscope is configured to be advanced within a body cavity of the patient.

11. The system according to claim 7, wherein the preoperative images are computed tomography (CT) images of the patient's lungs.

12. The system according to claim 7, wherein the computer is configured to acquire tissue data of the patient's lungs.

13. The system according to claim 7, wherein the endoscope includes a second camera.

14. The system according to claim 13, wherein the endoscope includes a light source.

15. The system according to claim 14, wherein the endoscope includes a structured light pattern source.

16. The system according to claim 15, wherein the topography of the patient's lungs is determined using the second camera, the light source, and the structured light pattern source.

17. A method of displaying an area of interest within a surgical site, comprising:
   instructing a processor associated with a computer to execute a software application, which when executed, creates a three-dimensional (3D) model of a patient's lungs from preoperative images;
   displaying real-time images of the patient's lungs captured by a first camera of an endoscope on a monitor associated with the computer, the first camera having a field of view; and
   instructing the processor to:
   generate a collapsed state 3D model of the patients lungs;
   determine a topography of the patients lungs;
   register the real-time images of the patient's lungs with the collapsed state 3D model of the patient's lungs using the determined topography of the patient's lungs; and
   superimpose, over the real-time images of the patients lungs, a marker indicative of a the location of the area of interest within the patients lungs as the area of interest appears in the collapsed state 3D model, a displayed position of the marker remaining stationary relative to the displayed real-time images of the patients lungs as the field of view of the first camera changes.

18. The method according to claim 17, further including displaying, when the area of interest is outside the field of view of the first camera, information on the monitor indicative of a direction in which the area of interest is located relative to the field of view of the first camera.

19. The method according to claim 17, wherein determining the topography of the patient's lungs includes determining the topography of the patient's lungs using a second camera, a light source, and a structured light pattern source associated with the endoscope.

20. The method according to claim 17, wherein instructing the processor associated with the computer to execute the software application includes acquiring computed tomography (CT) data and tissue data of the patient's lungs.

* * * * *